United States Patent

Falcone

[11] Patent Number: 5,980,456
[45] Date of Patent: Nov. 9, 1999

[54] EDIBLE TONGUE-DEPRESSOR AND THE LIKE

[76] Inventor: Carl L. Falcone, 1935 E. Military, Fremont, Nebr. 68025

[21] Appl. No.: 08/874,881

[22] Filed: Jun. 13, 1997

Related U.S. Application Data

[63] Continuation of application No. 08/505,826, Jul. 21, 1995, abandoned.

[51] Int. Cl.$^6$ ........................................................ A61B 11/02
[52] U.S. Cl. ............................................................. 600/240
[58] Field of Search .................................... 600/235, 240, 600/242, 210; 426/659, 660; D1/127, 128

[56] References Cited

U.S. PATENT DOCUMENTS

| | | | |
|---|---|---|---|
| D. 88,109 | 10/1932 | Reiche | D1/127 |
| D. 309,520 | 7/1990 | Thomassen et al. | D1/127 X |
| 2,857,908 | 10/1958 | Cornfield | 600/240 |
| 3,162,539 | 12/1964 | Repko | 426/659 |
| 3,315,664 | 4/1967 | Hill | 600/240 |

*Primary Examiner*—Beverly M. Flanagan
*Attorney, Agent, or Firm*—Zarley, McKee, Thomte, Voorhees & Sease

[57] ABSTRACT

The present invention discloses an edible tongue depressor and method of use which may be used for conducting examinations of a patient's oral cavity. The depressor is a generally elongated member having generally convex shaped top and bottom surfaces with sufficient rigidity to permit the depressing of a patient's tongue. The top and bottom surfaces may also comprise a series of ridges lending additional structural support. The depressors may be manufactured in a variety of flavors so that the patient can select his or her favorite. The invention also contemplates and edible tooth-pick and support stick for frozen deserts and the like.

7 Claims, 2 Drawing Sheets

EDIBLE TONGUE-DEPRESSOR AND THE LIKE

This application is a continuation application of U.S. Ser. No. 08/505,826, filed Jul. 21, 1995, now abandoned.

BACKGROUND OF THE INVENTION

1. Technical Field

The method and apparatus of the present invention relate generally to the use of an edible member to substitute for the purposes of conventional tongue depressors, toothpicks, or to support frozen desserts such as popscicles, ice cream bars or the like. More specifically, the present invention relates to the use of a member made of candy or other edible material. In this case, we refer to "edible" as something which is designed for the purpose of being eaten. One common example of such a material would be confection.

It is currently the case that during a medical examination given to a patient it is frequently necessary for the physician to accomplish a visual examination of the oral cavity. This is always the case when the patient visits the doctor's office complaining of a sore throat or other similar condition. In order for the doctor to accomplish a complete and thorough examination, he or she is required to depress the tongue from its normal, reflex position in order to expose the rear of the cavity. Normally, the tongue has a tendency to pivot upwardly when the mouth is opened, thereby obstructing the doctor's view of the throat cavity. Consequently, the doctor must depress the tongue while the patient opens his or her mouth so that adequate visibility of the entire throat cavity is permitted. An apparatus which performs this function is commonly referred to as a tongue depressor.

2. Description of the Prior Art

Currently, most tongue depressors are fashioned from wood. Typically, these pieces of wood are generally flat and smooth and of generally rectangular shape with rounded ends.

It is well understood by doctors using these conventional tongue depressors, and those to whom oral examinations are given, that such conventional tongue depressors have an extremely unpalatable taste. Furthermore, and even more disturbing, this unpalatable taste, in conjunction with the texture of the wooden tongue depressor, has a propensity to cause the gag reflex. This propensity is most pronounced in children. Clearly such a gag reflex interferes with the conduct of the examination. A more serious consequence of the unpleasantness of the examination would be a reluctance by a patient to seek treatment.

Additionally, the environmental impacts of the use of wood tongue depressors must be considered. While each individual depressor does not require much wood, when the total number of examinations given each day is considered, the amount of wood necessary is large.

Other implements have been suggested as substitutes for the conventional wooden tongue depressor. However, these heretofore suggested substitutes all suffer from similar or additional drawbacks. For example, the use of a stainless steel depressor has been suggested. However, while minimizing to some extent the gag reflex associated with wood, a stainless steel tongue depressor is relatively costly. Because of its relatively high cost, it is not economical to dispose of it after each use. Therefore, it would be necessary to re-sterilize the instrument before any reuse. Clearly, this necessitates considerable additional expenditure of time by the physician and/or assistants.

Consequently, it is a primary objective of the present invention to provide a tongue depressor does not suffer the drawbacks of prior art tongue depressors such as unpalatable taste and propensity to cause the gag reflex.

It is a further objective of the present invention to provide a tongue depressor which is made of any one of a number of types of confection.

It is a further objective of the present invention to provide a tongue depressor apparatus having sufficient rigidity to allow the tongue to be forcibly depressed during an oral examination.

It is a still further objective of the present invention to provide a tongue depressor of generally elongated construction.

It is a further objective of the present invention to provide a tongue depressor apparatus enclosed in a package having a perforation therein for easily releasing the tongue depressor therefrom.

It is a further objective of the present invention to provide an edible tongue depressor manufactured in a variety of confectionery flavors.

It is a further objective of the present invention to provide a tongue depressor which after the examination has been completed, may be either provided to the patient for consumption or alternatively readily disposed of.

It is a further objective of the present invention to provide a tongue depressor which does not contribute to the over-harvesting of trees.

A further objective of the present invention is to provide a tongue depressor which eliminates or greatly minimizes the gag reflex currently associated with conventional tongue depressors, thereby minimizing the reluctance of patients to come in for oral examinations.

It is a further objective of the present invention to provide an edible tongue depressor having a plurality of diagonal lines of increased thickness material to provide additional rigidity and strength thereto.

A further objective of the present invention is to provide an edible tongue depressor of increased environmental friendliness due to its ease of biodegradability.

It is further objective of the present invention to provide an edible tongue depressor having a slightly convex shape to better facilitate examination of the oral cavity while at the same time providing additional structural rigidity.

SUMMARY OF THE INVENTION

The present invention discloses an edible tongue depressor and method of use which may be used for conducting examinations of a patient's oral cavity. The depressor is a generally elongated member having generally convex shaped top and bottom surfaces with sufficient rigidity to permit the depressing of a patient's tongue. The top and bottom surfaces may also comprise a series of ridges lending additional structural support. The depressors may be manufactured in a variety of flavors so that the patient can select his or her favorite. The invention also contemplates and edible tooth-pick and support stick for frozen deserts and the like.

DESCRIPTION OF THE PREFERRED EMBODIMENT

Figure 1:
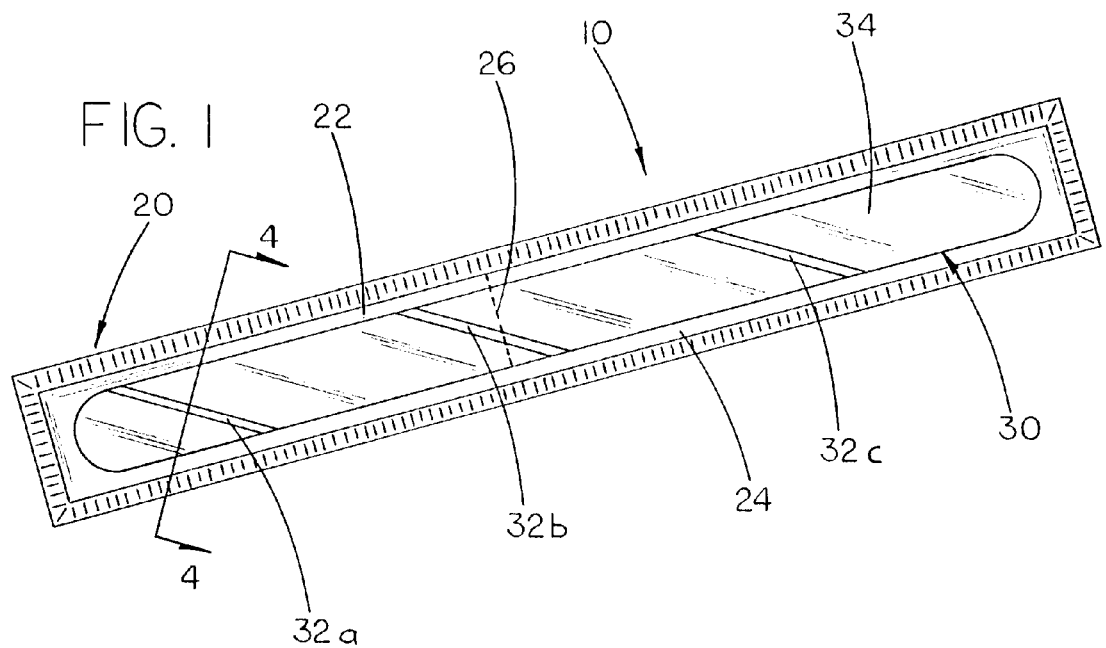
FIG. 1 is a perspective view of a preferred embodiment of the present invention showing the edible tongue depressor of the present invention enclosed in a clear plastic enclosure.
Figure 2:
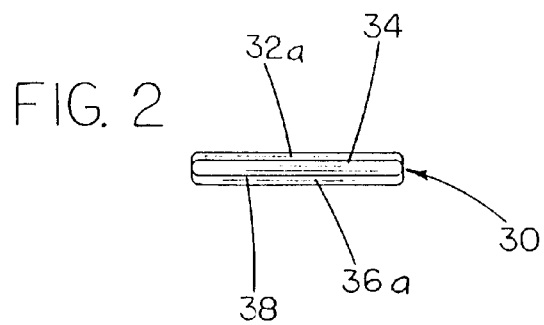
FIG. 2 is an end view of the edible tongue depressor apparatus of the present invention.
Figure 3:
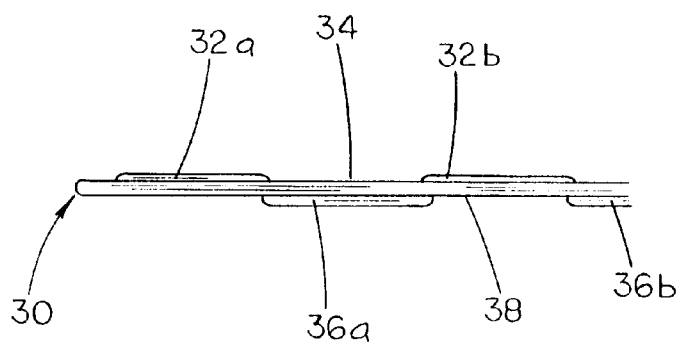
FIG. 3 is a side view of the edible tongue depressor apparatus of the present invention.
Figure 4:
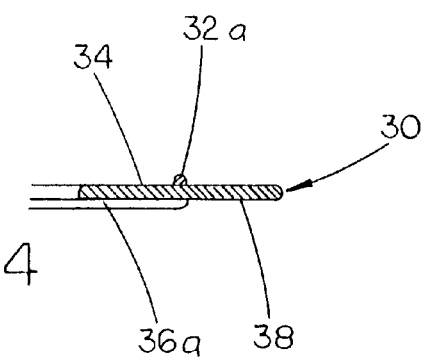
FIG. 4 is a cross sectional view taken along the lines shown in FIG. 1.

As mentioned above, there are three embodiments described by the present invention. The first and primary of these embodiments is the edible tongue depressor. The first alternative embodiment of the present invention is its use as an edible tooth pick. Finally, the second alternative embodiment is its use as a support stick member for popscicles or other frozen desserts.

The first, primary embodiment of the invention is illustrated in FIGS. 1 through 4. As seen from these figures, this primary embodiment comprises an elongated, semi-rigid, substantially thin member 30. It may be desirable to construct top and bottom surfaces 34 and 38 respectively with a sight convex shape adding additional structural rigidity and strength to member 30. In the preferred embodiment, this member 30 would be formed of some edible material. In one preferred embodiment, this edible material is some variety of confection. It is envisioned, that the edible tongue depressor could be manufactured using a wide variety of different flavors to have the widest possible appeal to the patients being examined. It is thought that with a wide variety of flavors, the examining physician could present a variety of tongue depressors to a patient allowing him or her to select the flavor to be used.

An important consideration in selecting the construction material and manufacturing process, is that the depressor must be given sufficient strength and rigidity to permit the physician to hold down the tongue while conducting the examination. It is felt that many varieties of confection would support such a function. Additionally, it is contemplated that the edible tongue depressor body 30 may also comprise a plurality of diagonally oriented ridges 32a–e and 36a–e on the top and bottom surfaces, 34 and 38 respectively of the depressor body 30. It is felt that this plurality of ridges 32a–e and 36a–e would provide additional strength and rigidity to the depressor without requiring a great deal of additional thickness to the depressor body 30 thereby keeping down the cost. As seen from the cross sectional view presented by FIG. 4, it is anticipated that these plurality of ridges 32a–e and 36a–e would be semi-circular in cross section. Obviously, other shapes and sizes could also be chosen.

It is envisioned that for purposes of sterility, the edible tongue depressor of the present invention would be enclosed in some type of package 20. In a preferred embodiment, the package 20 would comprise a clear plastic wrap completely enclosing the depressor body 30. This clear plastic packaging 20 would have a perforation 26 positioned approximately one-third of the length of the package from one end, dividing the package into a first portion 22 and a second portion 24. The perforation 26 would provide an easy means for the doctor or patient to remove the edible tongue depressor from its package. The use of a clear package 20 would permit the patient to readily identify the flavor of the edible tongue depressor and make his or her selection. Clearly other types of packaging may be equally suitable for use such as some type of more tightly wrapped packaging or even an opaque package with the flavor inscribed thereon.

As mentioned above, one of the major drawbacks from use of conventional wood tongue depressors are their propensity to cause the gag reflex thereby inhibiting examination of the patient. Use of the edible tongue depressor disclosed in the present invention will greatly minimize or eliminate this tendency thereby greatly facilitating the examination of the patient.

Additionally, in some situations it may be desirable to manufacture packaging 20 without a perforation 26. In this case, an alternative means for opening the package may be provided such as the use of an internal string adapted to cut the package as it is pulled outwardly, as is conventionally used in the packaging of items such as band-aids.

One possible material for the manufacture of the edible tongue depressor would be using a corn syrup base. As mentioned above, the objective is to provide a pleasant flavor while at the same time providing a substance and manufacturing technique which results in member 30 having sufficient structural rigidity and strength.

In addition to the use of the present invention in examination rooms by doctors or the like, the device may also be provided to nurses in settings such as schools thereby facilitating the timely and efficient examination of students.

As one possible suggestion for manufacturing the edible tongue depressors of the present invention, it is suggested that such tongue depressors may be manufactured using a mold such that when the curing of the stick is complete it may simply be popped out of the mold and packaged.

In addition to the reduction in the gag reflex which is usually associated with conventional wood tongue depressors, the edible tongue depressor of the present invention greatly diminishes the environmental impact due to the elimination of the need for wood.

While the preferred embodiment has been described as having a generally convex shape, it is also envisioned by the present invention that a generally flat shape could be utilized. It is anticipated that such a concave shape might add additional structural strength and rigidity to the depressor apparatus. However, if the material or process used to manufacturer the depressor is sufficiently strong, there is no reason member 30 could not be generally flat.

Figure 5:
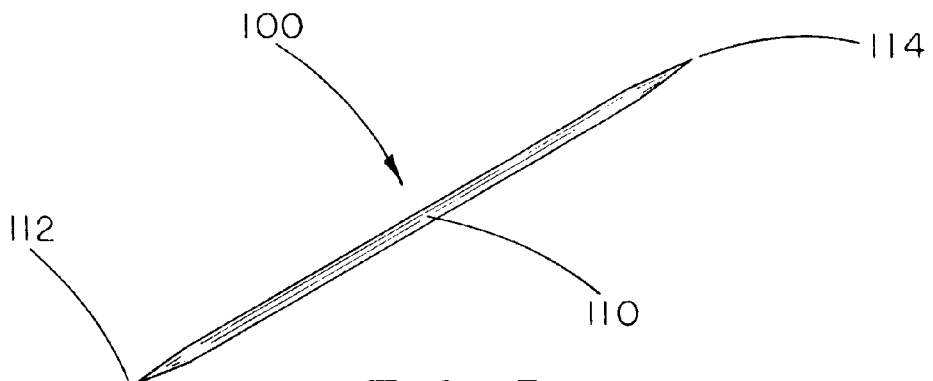
FIG. 5 is a perspective view of a first alternative embodiment of the present invention illustrating an edible toothpick according to the present invention.

The first alternative embodiment of the present invention is illustrated in FIG. 5. As mentioned above, this first alternative embodiment is a toothpick 100 manufactured using a confection similar to that employed in the manufacturer of the edible tongue depressor of the primary embodiment. In this embodiment, the toothpick comprises a main shaft 110 terminating on either end to sharp points 112 and 114. The toothpick 100 of this secondary embodiment would be manufactured of a confection similar to that employed with the tongue depressor with the main concern being that it be manufactured according to a process ensuring sufficient structural rigidity and strength so that the toothpick may be used in the usual manner.

Figure 6:
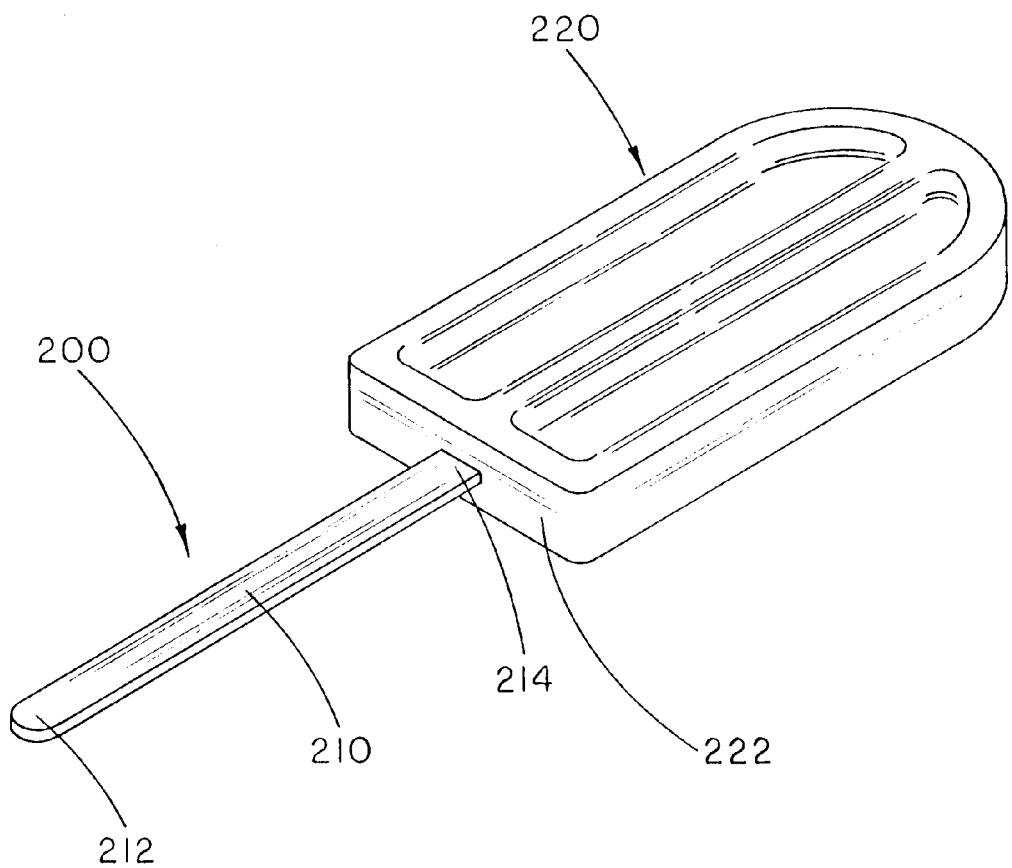
FIG. 6 is a perspective view of a second alternative embodiment illustrating the teachings of the present invention to construct an edible popscicle support stick.

The second alternative embodiment is illustrated in FIG. 6. In this second alternative embodiment, a support stick 200 for frozen desserts such as popscicles and the like would be constructed according to the process discussed above in connection with the edible tongue depressor. Namely, that stick 200 would be constructed of a confection material. In the preferred embodiment of this second alternative embodiment, the support stick 200 would comprise a main shaft 210 terminating in substantially flat ends 212 and 214. The stick 200 would have a shape very similar to the tongue depressor described above. As seen in the figure, one of the terminating ends, for example 214, would be inserted into the base 222 of popscicle body 220 during the manufacturing process. The support stick 200 would function in the normal manner that is provide a means for holding the frozen dessert during consumption. After the main frozen dessert has been consumed, the confectionery support stick 200 could either be eaten or disposed of. Clearly, manufacturing this sport shaft of an edible confection permits the ecological disposal thereof in a fashion much more ecologically friendly than use of a conventional wooden or paper support shaft.

It is obvious that numerous other modifications and variations of the present invention are possible in view of the above teachings. For example, the precise confectionery material used is not specified. This is because a large number of confectionery types would be equally suitable. Additionally the size and shape of the ridges suggested for additional structural support in the tongue depressor may be of numerous sizes and shapes or perhaps even eliminated. Furthermore, the packaging used to enclose the depressor may be of numerous designs.

Therefore it is to be understood that the above description is intended in no way to limit the scope of protection of the claims and is representative only of the several possible embodiments of the present invention.

There has thus been shown and described an invention which accomplishes at least all of the stated objects.

I claim:

1. An oral examination apparatus for depressing the tongue so as to permit careful and complete visual inspection of the oral cavity comprising:
    an elongated, semi-rigid, substantially thin member, having a thickness substantially less than its width and being formed entirely of edible material and being of a size insertable into a human mouth to permit the depressing of a tongue;
    wherein said elongated member comprises generally convex shaped top and bottom surfaces; and
    wherein said elongated member further comprises a plurality of ridges on said convex shaped top and bottom surfaces, said ridges being formed along the longitudinal length of said elongated member at predetermined locations, said ridges further being substantially semi-circular in cross-section, so as to provide additional strength and rigidity to said member without requiring a great deal of additional thickness to said member.

2. The oral examination apparatus for depressing the tongue so as to permit careful and complete visual inspection of the oral cavity of claim 1 wherein said elongated member is composed of confection.

3. The oral examination apparatus for depressing the tongue so as to permit careful and complete visual inspection of the oral cavity of claim 1 wherein said elongated member comprises rounded ends.

4. The oral examination apparatus for depressing the tongue so as to permit careful and complete visual inspection of the oral cavity of claim 1 further comprising package means operative to completely enclose said elongated member, said package means further comprising a perforation therein so as to permit separation of said package means along said perforation thereby exposing said elongated member for use.

5. A method of conducting an oral examination comprising the steps of:
    providing an oral examination tongue depressor having an elongated, semi-rigid, substantially flat and thin member being formed entirely of edible material and being of a size insertable into a human mouth to permit the depressing of a tongue, said elongated member comprising generally convex shaped top and bottom surfaces; and wherein said elongated member further comprises a plurality of ridges on said convex shaped top and bottom surfaces, said ridges being formed along the longitudinal length of said elongated member at predetermined locations, said ridges further being substantially semi-circular in cross-section, so as to provide additional strength and rigidity to said member without requiring a great deal of additional thickness to said member;
    inserting said tongue depressor into the mouth of a patient to be examined;
    depressing the tongue of a patient by placing said depressor on a patient's tongue and pressing downwardly;
    conducting the oral examination; and
    providing said depressor to a patient for consumption or disposal.

6. The method of conducting an oral examination of claim 5 wherein the step of providing a tongue depressor includes the step of providing a tongue depressor having a package means operative to completely enclose said elongated member, said package means further comprising a perforation therein so as to permit separation of said package means along said perforation thereby exposing said elongated member for use and wherein the step of providing the tongue depressor includes tearing said package along said perforation thereby exposing said tongue depressor for use.

7. The method of conducting an oral examination of claim 5 wherein the step of providing an oral examination apparatus comprises providing a plurality of examination apparatus, each of said examination apparatus comprising a different flavor the method further comprising the step of allowing a patient to select the tongue depressor to be used during the examination.

* * * * *